United States Patent [19]
Taylor

[11] Patent Number: 5,919,623
[45] Date of Patent: Jul. 6, 1999

[54] NUCLEIC ACID MUTATION ASSAYS

[75] Inventor: Graham Roy Taylor, Leeds, United Kingdom

[73] Assignee: St. James's and Seacroft University Hospitals NHS Trust, Leeds, United Kingdom

[21] Appl. No.: 08/740,309

[22] Filed: Oct. 28, 1996

Related U.S. Application Data

[63] Continuation of application No. PCT/GB95/00964, Apr. 27, 1995.

[30] Foreign Application Priority Data

Apr. 27, 1994 [GB] United Kingdom ............... 9408344

[51] Int. Cl.$^6$ ............... C12Q 1/68; C12P 19/34; A61K 38/43; C25B 1/00
[52] U.S. Cl. ............... 435/6; 435/91.2; 424/94.1; 204/182.8; 536/24.3
[58] Field of Search ............... 435/6, 91.2; 204/182.8; 536/24.3; 424/94.1; 530/350

[56] References Cited

U.S. PATENT DOCUMENTS

| | | | |
|---|---|---|---|
| 5,459,039 | 10/1995 | Modrich et al. | 435/6 |
| 5,556,750 | 9/1996 | Modrich et al. | 435/6 |

FOREIGN PATENT DOCUMENTS

| | | |
|---|---|---|
| 93/02216 | 2/1993 | WIPO . |
| 93/20233 | 10/1993 | WIPO . |
| 93/22457 | 11/1993 | WIPO . |
| 93/22462 | 11/1993 | WIPO . |
| 95/12688 | 5/1995 | WIPO . |

OTHER PUBLICATIONS

Su et al., *Escherichia coli*MutS–encoded protein binds to mismatched DNA base pairs, Proc. Natl. Acad. Sci. USA, vol. 83, pp. 5057–5061, 1986.

Lishanski et al., Mutation detection by mismatch binding protein, MutS, in amplified DNA: Application to the cystic fibrosis gene, vol. 91, pp. 2674–2678, 1994.

Ng et al. Mutational and In Vitro protein–binding studies on centromere DNA from *Saccharomyces cerevisiae*, vol. 7(12), pp. 4522–4534, 1987.

(List continued on next page.)

*Primary Examiner*—Kenneth R. Horlick
*Assistant Examiner*—Joyce Ting
*Attorney, Agent, or Firm*—Pillsbury Madison & Sutro, L.L.P.

[57] ABSTRACT

A method for detecting and locating mutations in DNA involves forming heteroduplex molecules by hybridizing single strands derived from a sample of target DNA under test with single strands derived from a sample of non-mutant reference nucleic acid so that any mutation causing an alteration in one or more nucleotide bases in the target DNA produces a base pair mismatch in the corresponding heteroduplex molecule. The nucleic acid mixture is then reacted with a mismatch-binding protein such as the mismatch repair enzyme Mut"S" which recognizes and binds to any such resultant mismatch site. Subsequent treatment with an exonuclease having unidirectional activity degrades duplex molecules free of mismatches but mismatch-containing heteroduplex molecules are protected by the mismatch-binding protein bound to the mismatch sited therein and this limits the extent of the exonuclease degradation. The degradation products are then analyzed, e.g. by get electrophoresis, to determine the size of residual single-stranded nucleic acid fragments and hence to establish the location of the mutation. This method has useful applications in medical diagnosis and biotechnology.

17 Claims, 6 Drawing Sheets

OTHER PUBLICATIONS

Proc. Natlacad. Sci., vol. 83, no. 14, Jul. 1986 Natlacad Sci. Washington, DC, UC;, pp. 5057–5061, S.–S. Su and P. Modrich "*Escherichia coli*mutS–encoded protein binds to mismatched DNA base pairs", cited in appln., see p. 5060, I.col,line 8–p. 5061,rt.col.,line2; figures 3,5.

Proc. Natlacad Sci.,vol.91,no.7, Mar. 29, 1994 Natlacad Sci., Washington,DC,US.; pp. 2674–2678,A. Lishanski et al. "mutation detection by mismatch binding protein, Muts, in amplified DNA: Application to the cystic fibrosis gene". the whole document.

Nucleic Acids Res. (1994), 22(13),2710–11, Soden:Narhad-;ISSN: 0305–1048, 1994, Ellis ,La. et al "MutS binding protects heteoduplex DNA from exonuclease digestion in vitro: a simple method for detecting mutations", the whole document.

J. Biolchem., vol 263, no 14, May 1, 1988 Am. Soc.Biochem.Molbiol, Inc., Baltimore,US;pp. 6829–6835;S.–S.SU et al "Mispair specificity of methyl–directed DNA mismatch correction in vitro". see p.6833,I col.line 20–p. 6834,rt col,line 22; figures 3,4.

FAM 5' AGC AAT GTT GTT TTT GAC CAA CTA

JOE 5' GCA CAG ATT CTG AGT ACC CAT AAT

FIG. 2

```
ATATACCCAT AAATATACAC ATATTTTAAT TTTTGGTATT TTATAATTAT  50

TATTTAATGA TCATTCATGA CATTTTAAAA ATTACAGGAA AAATTTACAT  100

Blue Primer
CTAAAATTTC AGCAATGTTG TTTTTGACCA ACTAAATAAA TTGCATTTGA  150

AATAATGGAG ATGCAATGTT CAAAATTTCA ACTGTGGTTA AAGCAATAGT  200

GTGATATATG ATTACATTAG AAGGAAGATG TGCCTTTCAA ATTCAGATTG  250

1717-1 G>A
AGCATACTAA AAGTGACTCT CTAATTTTCT ATTTTTGGTA ATAGGACATC  300

TCCAAGTTTG CAGAGAAAGA CAATATAGTT CTTGGAGAAG GTGGAATCAC  350

G551D(G>A)
S549N(G>A) R553X(C>T)
ACTGAGTGGA GGTCAACGAC CAAGAATTTC TTTAGCAAGG TGAATAACTA  400

ATTATTGGTC TAGCAAGCAT TTGCTGTAAA TGTCATTCAT GTAAAAAAAT  450

TACAGACATT TCTCTATTGC TTTATATTCT GTTTCTGGAA TTGAAAAAAT  500

CCTGGGGTTT TATGGCTAGT GGGTTAAGAA CACATTTAAG AACTATAAAT  550

Green primer (Reverse
AATGGTATAG TATCCAGATT TGGTAGAGAT TATGGTTACT CAGAATCTGT  600
Complement)
GCCCGTATCT TGG                                          613
```

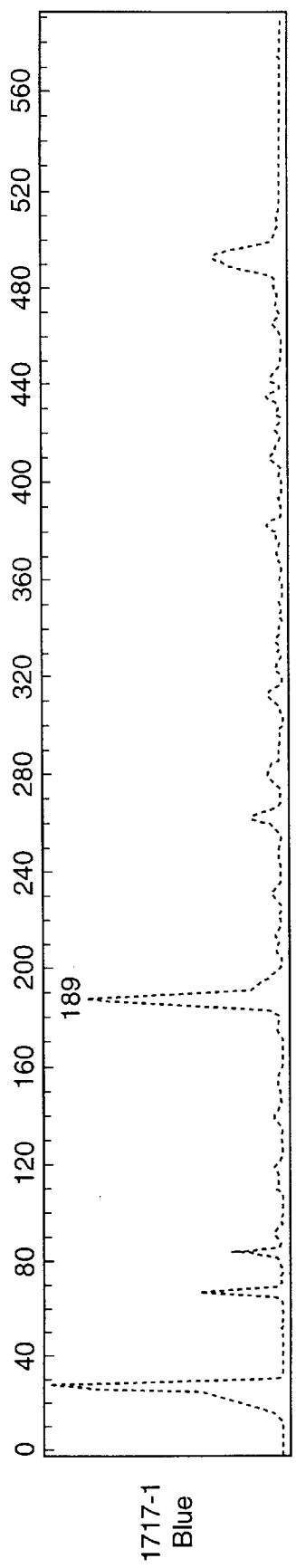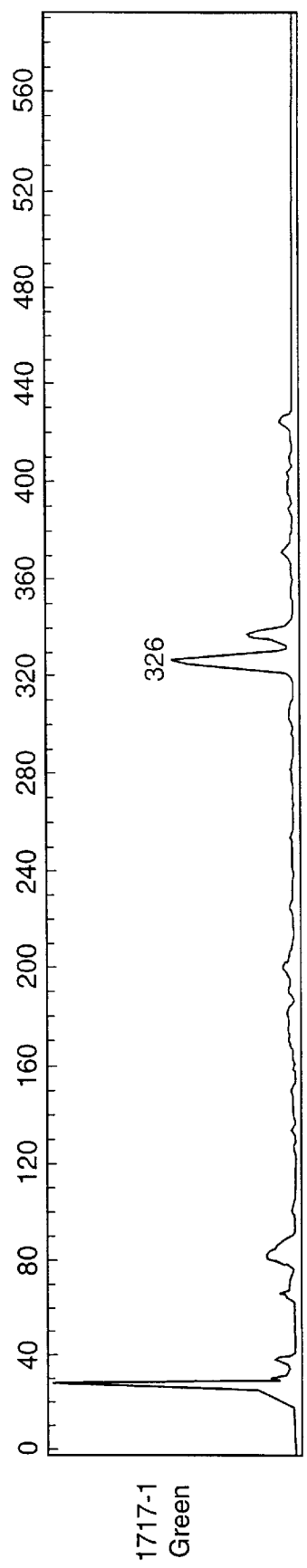

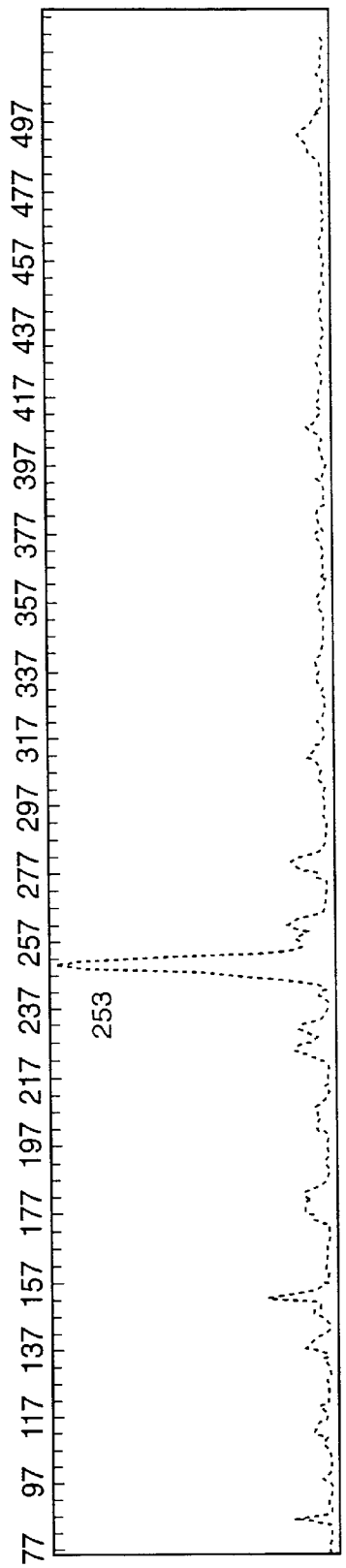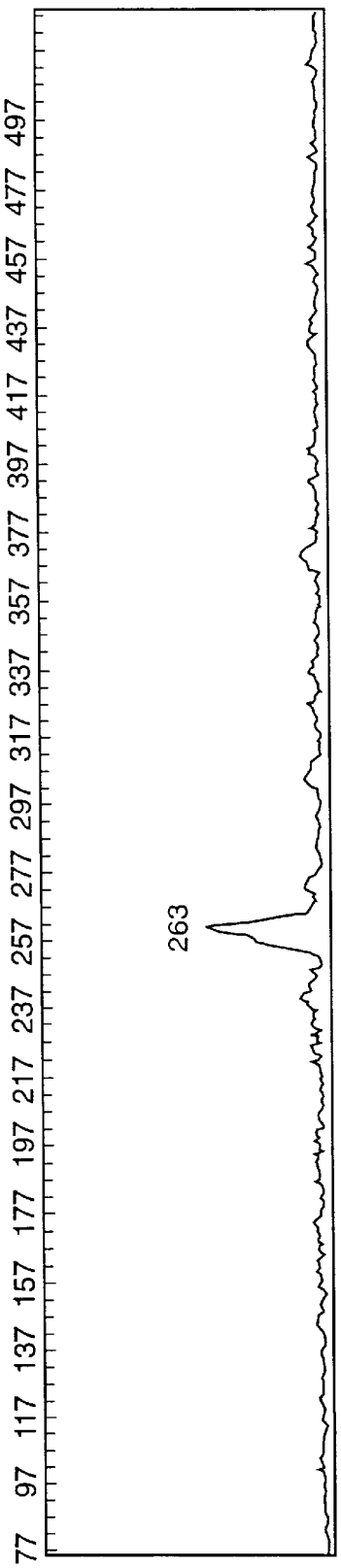

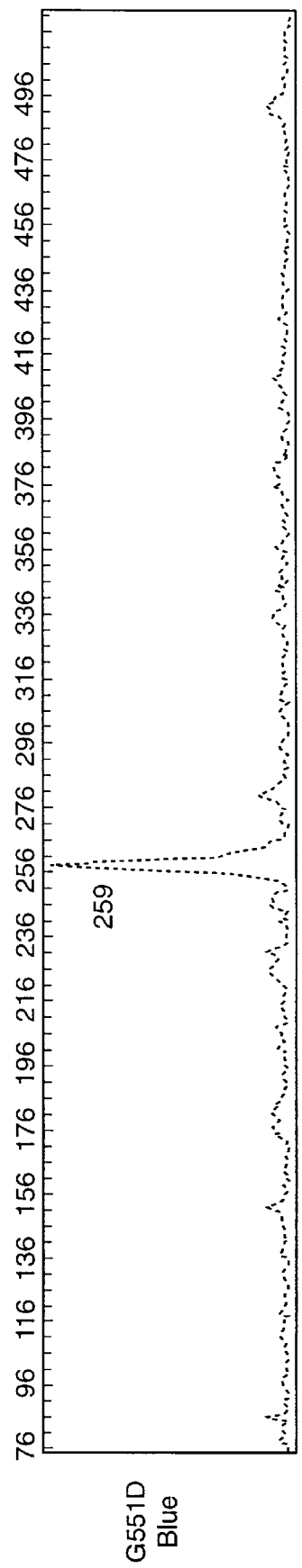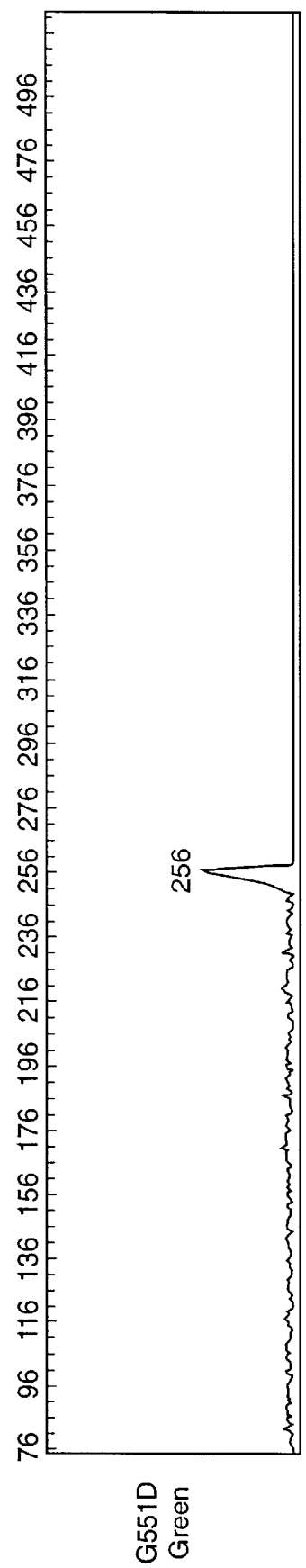

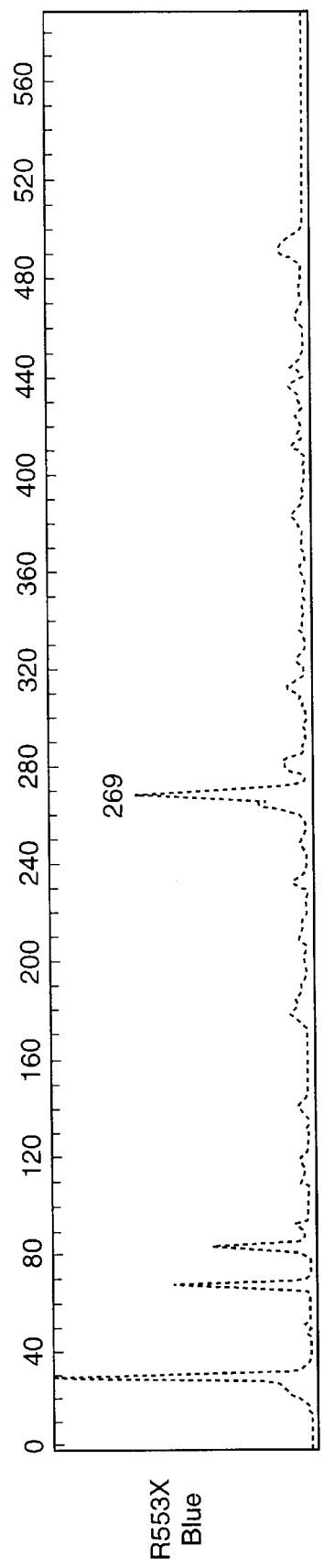
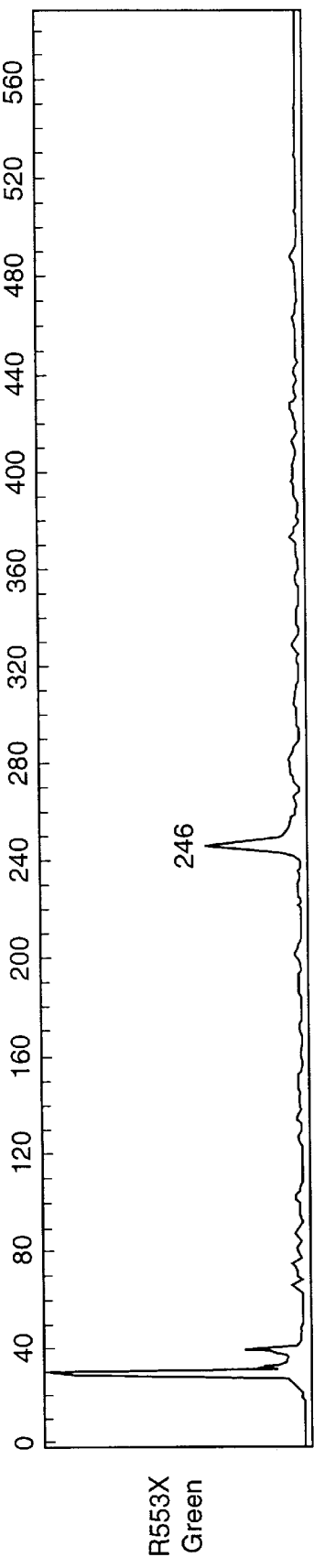
FIG. 7(a)
FIG. 7(b)

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:

(A) LENGTH: 613 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 1:

ATATACCCAT AAATATACAC ATATTTTAAT TTTTGGTATT TTATAATTAT TATTTAATGA     60

TCATTCATGA CATTTTAAAA ATTACAGGAA AAATTTACAT CTAAAATTTC AGCAATGTTG    120

TTTTTGACCA ACTAAATAAA TTGCATTTGA AATAATGGAG ATGCAATGTT CAAAATTTCA    180

ACTGTGGTTA AAGCAATAGT GTGATATATG ATTACATTAG AAGGAAGATG TGCCTTTCAA    240

ATTCAGATTG AGCATACTAA AAGTGACTCT CTAATTTTCT ATTTTTGGTA ATAGGACATC    300

TCCAAGTTTG CAGAGAAAGA CAATATAGTT CTTGGAGAAG GTGGAATCAC ACTGAGTGGA    360

GGTCAACGAC CAAGAATTTC TTTAGCAAGG TGAATAACTA ATTATTGGTC TAGCAAGCAT    420

TTGCTGTAAA TGTCATTCAT GTAAAAAAAT TACAGACATT TCTCTATTGC TTTATATTCT    480

GTTTCTGGAA TTGAAAAAAT CCTGGGGTTT TATGGCTAGT GGGTTAAGAA CACATTTAAG    540

AACTATAAAT AATGGTATAG TATCCAGATT TGGTAGAGAT TATGGTTACT CAGAATCTGT    600

GCCCGTATCT TGG                                                      613

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Oligonucleotide"

(xi) SEQUENCE DESCRIPTION: SEQ ID NO: 2:

AGCAATGTTG TTTTTGACCA ACTA                                           24

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Oligonucleotide"

(xi) SEQUENCE DESCRIPTION: SEQ ID NO: 3:

GCACAGATTC TGAGTACCCA TAAT                                           24

NUCLEIC ACID MUTATION ASSAYS

This is a Continuation of International Appln. No. PCT/GB95/00964 filed Apr. 27, 1995 which designated the U.S.

FIELD OF THE INVENTION

The present invention relates to the field of biochemistry and molecular biology, and is especially concerned with assays of nucleic acid for detecting and/or locating mutations therein, especially point mutations or insertion/deletion mutations involving the bases of just a few sequential nucleotides in, for example, the DNA of genes coding for proteins. Particularly in connection with this last aspect, the invention can have useful practical applications in biotechnology and medical diagnostics.

BACKGROUND

As is common knowledge, mutations can arise in sections of the nucleotide strands of genomic DNA either by deletion or insertion of part or all of a nucleotide base sequence or by an alteration of one or more nucleotide bases. Transcription from such mutated DNA sections ray then lead to defective protein products. Such defective protein products can be a cause of many genetic diseases or disorders. Such defective protein products that arise in fermentation processes in biotechnology may also be dysfunctional or harmful.

The ability to detect mutations in coding and non-coding DNA is important for the diagnosis of inherited disease. Nucleotide changes in a normal (i.e. wild-type) gene sequence are called gene mutations and can be either harmful or harmless. For example, a harmful gene mutation can be a single base pair change in a gene encoding an essential protein. A single base pair change or small insertion or deletion can result in a frame shift, a stop codon, or a non-conservative amino acid substitution, each of which can result in an inactive protein. A harmless gene mutation can be a gene polymorphism which results in a protein product with no detectable change in normal function. Mutation in non-coding DNA can also lead to disease, as in, for example, mutations in non-coding splice sites (found in certain cases of cystic fibrosis disease for instance) or mutations in transcriptional regulatory elements (found in certain defects of β-globin genes).

It is possible to form four sets of nucleotide mismatches when a mutant and normal DNA segment are annealed together. These sets include: G:A/C:T, C:C/G:G, A:A/T:T, and C:A/G:T. Each nucleotide pair represents eight possible single base pair mismatches which could be found in a DNA heteroduplex. However, DNA:RNA and RNA:RNA heteroduplexes can also be formed. Where a heteroduplex includes RNA, 9 single base pair mismatch sets are possible. DNA:DNA, DNA:RNA and RNA:RNA heteroduplexes can also be created by insertion or deletion of nucleotides in the mutant nucleic acid strand.

One example of a harmful mutation is provided by the well-known case of sickle cell anaemia where a point mutation involving an alteration of but a single nucleotide base, namely the substitution of a specific adenine by thymine in the genomic DNA, is responsible for the defect. In the case of cystic fibrosis the disease can arise from the presence of any one of a number of possible point mutations or small insertions or deletions that have been identified in different parts of the cystic fibrosis transmembrane regulator (CFTR) gene. Mutations in genomic DNA encoding oncogenes and tumour suppressors are also believed to be responsible for cell proliferation that causes many cancers.

Various methods of testing and detecting mutations in nucleic acids are known, many of which use for example a preliminary stage of polymerase chain reaction (PCR) amplification. Many of the existing methods are limited to cases where the precise nature and location of the mutation or molecular change being sought is already known and/or is of a particular kind. However, in many instances of disease-causing mutations the precise nature and location of the mutations are not known. A number of known methods of detecting unknown mutations in nucleic acids, such as SSCP, heteroduplex analysis, RNAse protection and chemical cleavage of heteroduplexes, are discussed in a review article by Markus Grompe entitled "The rapid detection of unknown mutations in nucleic acids" published 1993 in *Nature Genetics*, 5, 111–117. As yet there is no universal ideal method available and there is a need for more sensitive, rapid and efficient methods of detecting mutations in DNA. Such methods should also be capable of locating in a target nucleic acid or gene the position of point mutations or small mutations involving only a few bases.

When a mutation occurs in normal double stranded DNA of a living organism, initially this will generally affect one strand only of the duplex molecule, causing a mismatch in the base pairing. For example, with the occurrence of a point mutation a nucleotide cytosine base (C) in one strand may be changed so that the complementary quanine base (G) in the other strand becomes opposed to an adenine (A) or to a thymine base (T), producing a base-pair mismatch in the duplex molecule. However, certain proteins and enzymes, referred to as "proof-reading" proteins or enzymes or "DNA mismatch repair proteins or enzymes", are usually present in most living organisms and these enzymes act to detect such base-pair mismatches and to initiate a repair process in the mutated region before the molecules replicate and pass on the defect to subsequent copies of the DNA. One example of a set of such mismatch "repair enzymes", believed to be present in all living organisms, is provided by the Mut series of proteins and homologues thereof. A very well characterised system of these Mut repair enzymes, occurring for example in the bacterium *E.coli*, has been described by Paul Modrich and colleagues (for Review article, see for example Modrich, P. (1991), *Annual Rev. Genet.*, 25, 229–253), a set of three proteins having been identified and purified which are termed MutS, MutH and MutL. These detect errors in DNA replication by interacting with double-stranded nucleic acid molecules containing mismatched base pairs that arise when errors and new mutations occur. The DNA-repair protein MutS in particular is a highly conserved protein which has the ability to detect and bind to the sites of mismatched bases (other than C:C) or deletions or insertions of up to four bases (see for example paper by Shin-San Su and Paul Modrich, "*Escherichia coli* mutS-encoded protein binds to mismatched DNA base pairs" (1986) *Proc. Natl. Acad. Sci. U.S.A.*, 83, 5057–5061). MutS then recruits the MutH and MutL enzymes to create a nick at a CATG sequence near the mutation. Other enzymes then repair that region between the mutation and the nick (see also R. S. Lahue et al, "DNA Mismatch Correction in a Defined System" (1989) *Science* 245, 160–164).

The ability of various known mismatch repair enzymes to seek out and interact with mismatch regions in duplex DNA molecules has already led to some proposals for using such enzymes in assays to detect mutations responsible for such mismatches. Thus, in WO 93/02216 (Upstate Biotechnology, Inc., Lake Placid, N.Y., U.S.A.) a method for detecting mutations such as a single base change or an addition or deletion of about one to four base pairs in duplex nucleic acid molecules or polynucleotides is disclosed which is based on the use of a DNA mismatch-binding protein such as MutS in conjunction with a method using antibody reagents or the like for specifically recognizing or detecting the presence of said protein bound to nucleic acid or polynucleotide molecules. WO 93/20233 (University of Maryland at Baltimore) discloses a method for detecting single base pair mismatches at a preselected site in nucleic acids such as genomic DNA which is also based on the use of enzymes that repair mismatches in nucleic acids. In this latter method, however, mast emphasis is given to the detection of base pair mismatches at particular sites using mismatch repair enzymes having endonuclease activity that specifically cleave nucleic acid strands near to mismatches. Neither of the methods disclosed in the two above-mentioned patent publications, however, appear to be well-suited for determining the location of unknown mutations in nucleic acids, and in WO 93/02216 in particular the method appears to be concerned specifically with determining whether a particular sample of DNA includes a mismatch mutation without consideration of locating any such mutation that may be detected.

In a technique developed by Schmitz and Galas [Schmitz, A, and Galas, D. J. (1978) DNaseI footprinting: A simple method for the detection of protein-DNA binding specificity." *Nucleic Acids Research,* 5, 3157–3170] for the study of sequence-specific binding of proteins to DNA, a DNA fragment is exposed to a sequence-specific DNA binding protein. After such time as to allow for binding, the protein-DNA complex is treated with DNaseI. The bound protein shields that region of DNA to which it is bound from digestion by DNaseI, and after separation of the reaction products by gel electrophoresis, the protected region is seen as a gap in the otherwise continuous background of digestion products.

Footprint analysis has also been accomplished using DNA digesting enzymes which are processive, i.e. act on the DNA in a 3' to 5' fashion. The prototype enzyme which has been used for this type of assay is Exonuclease III. The procedure for such exonuclease footprinting involves binding of sequence specific DNA binding protein to the DNA followed by exonuclease digestion. As with the above-mentioned technique using DNase, the bound protein protects the DNA from digestion. , due to the processive nature of the exonuclease, the reaction products do not consist of a background of randomly cleaved DNA fragments, rather they consist of two single stranded species which overlap and form double standed DNA only in the region of the DNA-protein interaction. Thus, after separation by gel electrophoresis, the region of DNA-protein interaction may be deduced by the lengths of the two single stranded reaction products.

It is to be noted, however, that in none of the aforementioned prior art has there been any disclosure of a footprinting or similar technique involving endonucleases or exonucleases being used to detect mutations in DNA.

SUMMARY OF THE INVENTION

Insofar as the present invention in its main aspect concerns assays to detect mutations or base mismatches occurring in nucleic acid molecules, it is based on a principle of forming heteroduplex nucleic acid molecules in which strands derived from an original nucleic acid test sample are paired with non-mutant strands from a corresponding reference sample. Said reference sample may, for example, be provided by the wild-type non-mutated nucleic acid or derivative thereof, for example a cloned DNA or amplified PCR derivative or an equivalent synthetic oligonucleotide. A mismatch-binding protein or repair enzyme, such as the MutS protein or homologues thereof for example, or other mismatch-binding protein(s) as herein disclosed, is then used to seek cut and bind to any relevant mismatch site in the heteroduplex molecule resulting from point mutations or from insertions or deletions of a few sequential nucleotide bases in the strands from the test sample. Upon then digesting the reaction mixture with an exonuclease all the nucleic acid molecules without any mismatches or small insertions or deletions are digested and completely removed. Heteroduplex molecules containing mismatches or small insertions or deletions will be detectable because the bound protein acts to block-the exonuclease and protect the underlying strands from its action. Thus, residual single strand fragments will only be derived from the mismatch-containing hetero-duplex molecules. Analysis of these single strand fragments can then enable the locus of the mismatched bases to be determined.

In a particularly preferred procedure the DNA protected by the bound mismatch-binding protein or repair enzyme is detected by digesting the nucleic acid reaction mixture with an exonuclease enzyme having a specific unidirectional exonuclease activity, under conditions in which the exonuclease enzyme progressively removes or deletes nucleotides from one end of each nucleic acid strand until reaching the site of a base-pair mismatch bound to the mismatch-binding protein or repair enzyme. The latter then blocks and protects against further exonuclease digestion along the strand. For such heteroduplex DNA molecules containing a mutation and mismatch of bases there is therefore no complete degradation by the exonuclease enzyme, and the presence of incompletely degraded relatively large DNA fragments can then be detected by various methods. By then determining the size of the fragments the location of the mismatch region and of the mutation may also be ascertained.

Thus, according to one aspect the invention provides a method for detecting a mutation in a test sample of target nucleic acid, said method comprising a) providing a control sample of reference nucleic acid capable of hybridizing to strands of the target nucleic acid from said test sample;

b) denaturing if necessary said reference nucleic acid and said target nucleic acid, or replicates thereof, forming single-stranded reference nucleic acid and single-stranded target nucleic acid;

c) annealing said single-stranded reference nucleic acid and said single-stranded target nucleic acid, wherein said annealing is sufficient to form heteroduplex nucleic acid composed of one strand derived from said target nucleic acid hybridized with a second strand derived from said reference nucleic acid;

d) contacting said heteroduplex nucleic acid with a mismatch-binding protein capable of binding selectively to the site of said mutation;

e) treating said annealed nucleic acid material with an exonuclease, the presence of said mismatch-binding protein being sufficient to protect said nucleic acid to which it is bound from digestion by said exonuclease; and f) detecting the presence of said protected nucleic acid as a indication of the presence of said mutation in said target nucleic acid.

In preferred embodiments the method further comprises determining the length of residual strand fragments of said protected nucleic acid, giving an indication of the location of said mutation. The determination of the length of such residual strand fragments, or size resolution and analysis thereof, is preferably carried out by gel electrophoresis, e.g. polyacrylamide gel electrophoresis (PAGE), of the denatured nucleic acid exonuclease digestion products whereby the nucleic acid fragments are separated according to their relative size. For detecting and visualising the size separated fragments in the gel a suitable label (e.g. a fluorescent dye or radioactive agent) may be incorporated at an earlier stage into the reference nucleic acid molecules, or suitable labelled probes and Southern blotting for example may be used where sufficient sequence information is already available in respect of the expected fragments from particular mutations. Other alternative size separation methods or techniques, however, may also be used if desired, including for example capillary electrophoresis, size exclusion chromatography, high performance liquid chromatography (HPLC) and thin layer chromatography (TLC).

The invention also provides a method for detecting single base mismatches or mutations in nucleic acid comprising the steps of (a) generating heteroduplex nucleic acid molecules in which single strands derived from a sample of the target nucleic acid under test are hybridized with corresponding non-mutant single strands derived from a reference nucleic acid sample whereby mutant strands present in the original target nucleic acid test sample become paired with non-mutant-strands from the reference nucleic acid sample to form mismatch-containing heteroduplex nucleic acid molecules;

(b) contacting the nucleic acid material generated in step (a) with a mismatch-binding protein effective to seek out and selectively bind to mismatch sites in the heteroduplex molecules;

(c) digesting the nucleic acid material from step (b) with an enzyme having exonuclease activity whereby said enzyme progressively removes or deletes nucleotides from one end of each strand of the heteroduplex molecules until encountering said mismatch-binding protein bound to a mismatch site, said protein then acting to block further deletions and strand degradation by the exonuclease enzyme; and (d) analysing the nucleic acid digestion products from step (c) to determine the size or sizes of remaining single stranded nucleic acid fragments.

The presently preferred mismatch-binding protein for use in carrying out the invention is a MutS encoded protein such as the commercially available E.coli MutS protein from the Mut repair protein series. This is effective, albeit with somewhat different affinities, to bind to mismatch regions produced by most of the different possible base mismatch pairings within a range of one to about four nucleotides. Other mismatch-binding proteins or repair enzymes, however, may also be used. These may be similar to or homologues of the above-mentioned MutS protein and will have equivalent characteristics insofar as the detection and binding to mismatch regions of interest in heteroduplex DNA molecules is concerned and ability to protect nucleic acid strands to which they are bound against exonuclease digestion. Such other mismatch-binding proteins include, for example, HexA, from *Streptococcus pneumoniae*, MutS from *Salmonella typhimurium*, MutS from *A. Vinlandii*, MSH 1 from *Saccharomyces cerevisiae*, HMSH2 from humans, MMSH2 from mouse, XMSH2 from Xenopus, and p160 from humans Various exonucleases or DNA polymerases containing exonuclease activity may be used for the digestion stage, including exonuclease III, T4 DNA polymerase, Vent (Polve) polymerase, bacteriophage lambda exonuclease and T7 DNA polymerase. The presently preferred enzyme, however, is T7 DNA polymerase which has a specific processive 3' to 5' exonuclease activity.

In carrying out the invention, the original target nucleic acid of the test sample and also the reference nucleic acid will usually first be subjected to amplification either by cloning or, more conveniently, by using a conventional PCR amplification technique with appropriate primers and a high fidelity Taq polymerase.

In preferred embodiments, the reaction mixture containing the heteroduplex nucleic acid molecules is treated with the mismatch binding protein such as the MutS protein under slightly alkaline conditions, most preferably in the pH range of 8.0 to 8.5, and in the presence of a divalent cation such as $Mg^{++}$ which should normally be at a concentration of at least 7 mM, and preferably at a concentration of about 8 mM. The temperature, however, at which the treatment with the mismatch binding protein is carried out is not usually critical, at least not with MutS, and may be within the range of about 0° C. to about 30° C. for example.

For marketing and practical use, all the basic essential materials and reagents required for carrying out the detection method of the present invention may be assembled together in a self-contained kit. Such kits thus provide another aspect of the invention. Such kits will include one or more mismatch-binding proteins or repair enzymes capable of seeking out and binding to mismatch sites in heteroduplex molecules and an enzyme having specific unidirectional exonuclease activity, each reagent being in a separate container comprised within the kit, together with appropriate buffer and instructions for use. Assuming optional PCR amplification is to be used such kits may also include preselected primers, preferably detectably labelled, for PCR amplification of a particular fragment of a specific nucleic acid sequence or gene, Taq polymerase enzyme, a mix of deoxynucleotides and buffers to provide the necessary reaction mixture for carrying out selective PCR amplification.

The invention also provides a method for screening or testing human or animal subjects for the presence of a suspected genetic defect or mutated gene related disease, said method comprising obtaining nucleic acid from said subject and using that nucleic acid as the target nucleic acid in carrying out a method of detecting and localising a mutation as herein disclosed.

The original target nucleic acid of the test sample will generally comprise double-stranded genomic or cloned DNA or may be cDNA derived possibly from mRNA. The reference nucleic acid providing a control saddle will also frequently be provided by a fragment of double-stranded DNA, particularly non-mutated wild-type genomic DNA, or cloned DNA or cDNA, or even a synthetic oligonucleotide, all of which varieties are to be regarded as being covered by, and included within, the term "nucleic acid" as used herein.

The invention, and an example of the manner in which it may be carried cut in practice to detect mutations in genomic DNA, will now be described in more detail with reference to the accompanying drawings.

BRIEF DESCRIPTION OF THE DRAWINGS

FIG. 2 illustrates the nucleotide base sequence (SEQ ID NO: 1) of a fragment of the human cystic fibrosis transmembrane regulator (CFTR) gene containing, between flanking sequences, the CFTR exon 11 (GenBank accession number M55116) in which the locations of four known but different alternative point mutations, designated 1717-1 G>A, S549N, G551D and R553X respectively, are indicated;

FIG. 3 shows the base sequence of fluorescent labelled synthetic oligonucleotide priers used for PCR amplification of a 492 base pair (bp) sequence of the genomic DNA fragment depicted in FIGS. 2, 3(a) being the sequence (SEQ ID NO: 2) of one primer that is labelled with a blue fluorescent dye (designated FAM) and 3(b) being the sequence (SEQ ID NO: 3) of the second primer which is complementary to the sequence at the other end of the selected 492bp fragment and which carries a label consisting of a green fluorescent dye (designated JOE);

FIGS. 4(a) and 4(b) illustrate the detection of the 1717-1 G>A mutation in the CFTR exon 11 sequence indicated in FIG. 2 after subjecting a PCR amplification product thereof, obtained using the primers of FIG. 3, to a method of mutation detection in accordance with the present invention, this method involving digestion of the PCR product that contains mutation mismatch heteroduplex molecules with a MutS mismatch-binding protein or repair enzyme, followed by degradation with a 3' to 5' exonuclease, size separation of the resulting DNA fragments by denaturing polyacrylamide gel electrophoresis, and then optically detecting the fluorescent dye label of relevant fragments, wherein (a) represents the spectrum obtained in relation to the FAM primer carrying the blue fluorescent label on one strand and (b) represents the spectrum obtained in relation to the JOE primer carrying the green fluorescent label on the complementary strand; and FIGS. 5(a) and 5(b), 6(a) and 6(b), and 7(a) and 7(b) are each two part diagrams corresponding to FIG. 4 but illustrating respectively the detection of other mutations S549N, G551D and R553X.

DETAILED DESCRIPTION

Figures 1, 3A, 3B:
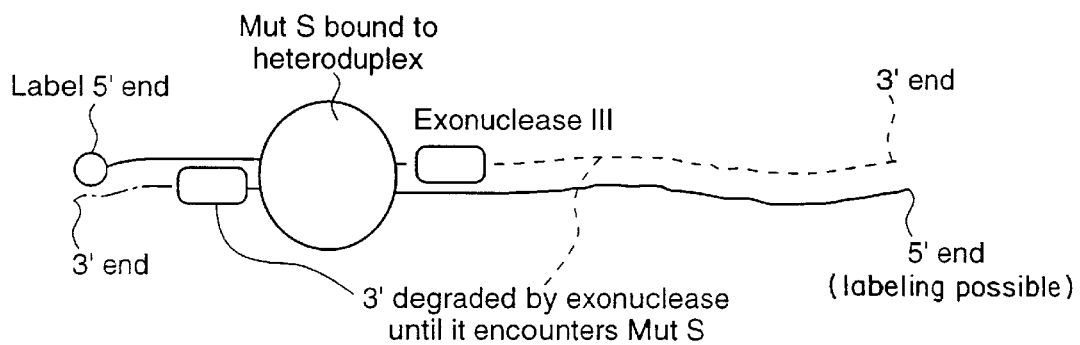
FIG. 1 is an annotated diagram illustrating the general principle involved in using a MutS DNA mismatch-binding protein or repair enzyme to detect and bind to a nucleic acid duplex molecule at the location of a base pair mismatch, and in then digesting the nucleic acid with an enzyme having a specific 3'–5' exonuclease activity in order to enable the MutS binding subsequently to be detected and located by resolving and separating the residual single stranded fragments according to size using, for example, denaturing gel electrophoresis.

In FIG. 1 a MutS mismatch-binding protein or repair enzyme is diagrammatically depicted bound to a mismatch region of a heteroduplex nucleic acid molecule which is suitably labelled at the 5' end of at least one strand, and an enzyme having a specific 3' to 5' exonuclease activity is depicted on each strand while progressively degrading the latter from their 3' ends prior to a subsequent stage of analysis to resolve and separate the nucleic acid strand fragments according to size.

In the specific example to which FIGS. 2 to 7 of the drawings relate, the invention was tested by being used to detect commonly occurring known mutations in exon 11 of the human cystic fibrosis transmembrane regulator (CFTR) gene which provides a test model for evaluating the method.

A 492 base pair DNA amplification product of the CFTR gene was generated first by PCR using synthetic oligonucleotide primers (purchased from Applied Biosystems) having the nucleotide sequences (SEQ ID NO: 2 and SEQ ID NO: 3) shown in FIG. 3 and labelled with blue and green fluorescent dyes, these being designated FAM and JOE respectively. Using the above-mentioned fluorescent primers under standard PCR conditions, as described for example in the paper entitled "Primer-directed enzymatic amplification of DNA with a thermostable DNA polymerase" by Saiki et al (1988) Science 239, 487–91, using 58° C. annealing temperatures and a high fidelity Taq polymerase (Perkin-Elmer Ampitaq™ N801-0060), thirty cycles of amplification were carried out from an initial sample of human genomic DNA made up of wild type reference DNA and target DNA in approximately equal amounts. The wild type reference DNA had a sequence corresponding to FIG. 2 without mutations (standard DA), whilst the target DNA being tested (obtained from human patients afflicted with cystic fibrosis) had a sequence corresponding to FIG. 2 but containing one of the four different mutations indicated therein. This produced samples of amplified DNA labelled with FAM at one end and JOE at the other end of the molecule.

The "standard" PCR conditions referred to above comprised denaturing for 5 minutes at 93° C., then performing 30 cycles each comprising successive temperature levels of 95° C. for 1 minute, 58° C. for 1 minute and 72° C. for 1 minute. Final extension was at 72° C. for 5 minutes. Buffer was Tris (pH 8.4) 10mM, KCl 50mM, $MgCl_2$ 1.5mM, dNTP 200uM. Of the primers, 50 pmoles each were used in a 50 $\mu$l reaction mixture. Human genomic DNA used was 50ng in a 50 $\mu$l volume of reaction mixture. Taq polymerase was used at 1 unit per 50 $\mu$l reaction mixture.

The PCR products were then purified by centrifugal microfiltration or dialysis using Centricon™ 100 tubes (Amicon) which removed excess primers and other reagents. In each case the PCR product (50 $\mu$l) was diluted to 2 ml in TE buffer, pH 8, and concentrated to a final volume of 25–30 $\mu$l. The final wash used exonuclease buffer (50mM Tris, pH 7.5, 7mM $MgCl_2$, 5mM DTT), and the DNA content of the purified PCR product was determined by measurement of the optical density at 260 nm (OD 260). It may be noted that subsequent heteroduplex formation occurs better in the absence of Taq polymerase, so the Centricon step was included to remove this and other PCR reagents. Thus no new DNA synthesis occurs which might interfere with heteroduplex formation.

The PCR product (20 $\mu$l to 30 $\mu$l) in 100mM NaCl, 10mM Tris (pH 7.5) and 1mM EDTA, was then heated to 95° C. for five minutes, followed by cooling to 65° C. over a 60 minute period so as to promote the formation of heteroduplex molecules by hybridization of one strand of the non-mutant wild type DNA with a strand of the test DNA that contains a mutation. This heteroduplex formation was also carried out in exonuclease buffer, i.e. 50mM Tris, pH 7.5; 7mM $MgCl_2$, 5mM dithiothreitol. The reaction mixture containing the heteroduplex molecules thus formed was then either used immediately or stored at −20° C. until use.

2 pmole (1–5 pmole ranges seem to work) of the DNA mixture containing the heteroduplex molecules produced (expected to be 50% heteroduplex, 50% homoduplex) was then treated in the next stage with a preparation of the MutS protein to promote binding of the latter to the heteroduplex molecules at the site of mismatched bases. In more detail, 5 pmoles of MutS protein (purchased from United States Biochemicals Ltd.—catalogue number 71422—and stored at −20° C. until use), 5 $\mu$l of dilution buffer (containing 50mM Hepes, 100mM KCl, 1mM EDTA, and 1mM DTT) was mixed and incubated on wet ice for 1 hour with the 2 pmoles of the DNA in 15 $\mu$l of buffer (pH 7.5) containing 50mM NaCl, 10mM Tris-Cl, 7mM $MgCl_2$ and 1mM EDTA made up to a total final volume 20 $\mu$l (subsequently, it has been found that a higher pH in the range of 8 to 8.5, preferably 8.5, can be beneficial, and that the $Mg^{++}$ concentration may advantageously be increased to 8mM. Also, the MutS binding can be performed if desired at higher temperatures, for example at least up to about 30° C.). After incubation on wet ice for 1 hour, 10 units of T7 polymerase (a processive exonuclease obtained from New England Biolabs—catalogue number 256S) were added and the tube was transferred to a 37° C. waterbath. The actual amount of T7 polymerase used has varied in different experiments between 5 and 10 units, but generally better signal- to-noise ratios have been seen using 10 units. After digestion for 3–5 minutes, this time being judged sufficient to ensure complete degradation of all duplex DNA molecules free of mutations and therefore not bound to the MutS protein, the reaction was stopped by the addition of 10 µl gel loading buffer (deionised formamide containing 10mM EDTA). The samples were heated to 90° C. to denature the DNA and were then loaded, together with reference standards of known size (Applied Biosystems Rox 2500), onto a polyacrylamide sequencing gel (6% concentration, containing 7M Urea) for analysis.

In this example the apparatus used for analysis was a model 373 automated DNA sequencer of Applied Biosystems Inc. using Applied Biosystems 672 Genescanner™ software. This gave the results which are illustrated in FIGS. 4 to 7 and which are summarised in Table 1 at the end of the present description, fragment sizes being estimated using a third order least squares approximation. As will be seen from FIGS. 4 to 7, in this example distinct peak were visible on both strands which were absent in control samples, and a good signal to noise ratio was obtained although some small background peaks were present.

The assay carried out substantially as described above has also been evaluated by testing other known mutations of the CFTR gene and thus far it has been shown to be capable of detecting also the mutations G85E, R75X, R75Q and P67L in CFTR exon 3.

It will of course be appreciated that in modifications of the method as described in the example above autoradiographic or other gel detection techniques could alternatively be used in carrying out the analysis provided they have sufficiently high resolution characteristics. Also, as already indicated, other size separation methods (particularly capillary electrophoresis, but also for example size exclusion chromatography, HPLC and thin layer chromatography) could readily be adapted to carry out the size separation process after the exonuclease treatment, if so desired. In addition, other labelling methods which could be used include the use of radiolabelled primers or PCR products, or instead of labelling the nucleic acid strands before digestion with the exonuclease enzyme silver staining or any other suitable DNA detection methods could be used to detect the DNA fragments after digestion and electrophoresis.

The best exonuclease activity found so far has been seen with the exonuclease activity of T7 DNA polymerase which is the presently preferred enzyme as previously mentioned, but other enzymes with processive, preferably unidirectional, exonuclease activity (either 3'–5' or 5'–3') can also be suitable. In particular it may be found advantageous to use lambda exonuclease or Vent polymerase (Pol-ve) available from New England Biolabs.

Although the MutS enzyme is presently the preferred mismatch-binding protein, other mismatch-binding proteins could also be used which may provide greater stability, including homologues of MutS, for example the human MutS homologue hMSH2, or in some cases it may be found advantageous to use mixtures of Mut proteins or other mismatch-binding proteins. It may also be possible as another advantageous alternative to use proteins which are not necessarily involved in repair of mutations but which nevertheless have a similar strong binding affinity specifically for base pair mismatch regions of nucleic acid molecules, for example the so-called Holiday junction binding RuvC protein from E. coli. If desired, genetic engineering techniques such as site directed mutagenesis may also be employed to modify artificially MutS protein or homologues thereof so as, for example, to increase stability or improve sensitivity and binding characteristics. Also, in a further modification, stability of the heteroduplex molecules carrying the MutS or other mismatch-binding protein bound thereto may be improved by treatment with a chemical cross-linking agent, e.g. formaldehyde, before commencing the treatment with the exonuclease, thereby to cause the protein to be bound even more strongly for resisting and blocking the action of the exonuclease.

Various other modifications are of course also possible within the scope of the invention which includes all novel and inventive features and aspects herein disclosed, either explicitly or implicitly and either singly or in combination with one another. In particular, the scope of the invention is not to be construed as being limited by the illustrative examples or by the terms and expressions used herein merely in a descriptive or explanatory sense.

TABLE 1

| Mutation | Observed fragment size (blue) | Distance from primer to mutation (blue) | Observed fragment size (green) | Distance from primer to mutation (green) |
|---|---|---|---|---|
| wild type | none | NA | none | NA |
| 1717-1 G > A | 189 | 184 | 326 | 307 |
| S549N | 253 | 245 | 263 | 246 |
| G551D | 259 | 250 | 256 | 241 |
| R553X | 269 | 256 | 246 | 235 |

I claim:

1. A method for detecting and locating a mutation in a test sample of double-stranded target nucleic acid, said method comprising:
   a) providing a control sample of reference nucleic acid which hybridizes to strands of the target nucleic acid from said test sample;
   b) denaturing said reference nucleic acid and said target nucleic acid, or replicates thereof, to an extent sufficient to form single-stranded reference nucleic acid and single-stranded target nucleic acid;
   c) annealing said single-stranded reference nucleic acid and said single-stranded target nucleic acid, wherein said annealing is sufficient to form heteroduplex nucleic acid composed of one strand derived from said target nucleic acid hybridized with a second strand derived from said reference nucleic acid;
   d) contacting said heteroduplex nucleic acid with a mismatch-binding protein that binds selectively to the site of said mutation to obtain an annealed nucleic acid material;
   e) treating and digesting said annealed nucleic acid material with an exonuclease, the presence of said mismatch-binding protein being sufficient to protect a nucleic acid molecule to which it is bound from complete degradation by said exonuclease, said treatment with said exonuclease being continued until the exonuclease reaches the site of the mismatch-binding protein or, in the event of there being no mismatch-binding protein, until the nucleic acid molecule is completely degraded; and f) detecting the presence and location of protected nucleic acid as an indication of the presence and location of said mutation in said target nucleic acid.

2. The method of claim 1, wherein subsequent to step (e) said method further comprises determining the length of residual strand fragments of said protected nucleic acid as an indication of the location of said mutation.

3. The method of claim 2 wherein the determination of the length of said residual strand fragments of the protected nucleic acid is carried out by gel electrophoresis of denatured nucleic acid digestion products from step (e) whereby said residual strand fragments are separated according to their relative sizes.

4. The method of claim 2 wherein the method used for determining the length of said residual strand fragments of the protected nucleic acid is selected from the group consisting of capillary electrophoresis, size exclusion chromatography, high performance liquid chromatography (HPLC) and thin layer chromatography (TLC).

5. A method for detecting and locating single base pair mutations in double-stranded target nucleic acid molecules comprising the steps of (a) generating heteroduplex nucleic acid molecules in which single strands derived from a denatured sample of the target nucleic acid molecules under test are hybridized with corresponding non-mutant single strands derived from a reference nucleic acid sample whereby mutant strands present in the original target nucleic acid test sample become paired with non-mutant strands from the reference nucleic acid sample to generate nucleic acid material containing mismatch-containing heteroduplex nucleic acid molecules;

(b) contacting the nucleic acid material generated in step (a) with a mismatch-binding protein effective to seek out and selectively bind to mismatch sites in the heteroduplex molecules;

(c) digesting the nucleic acid material from step (b) with an enzyme having exonuclease activity whereby said enzyme progressively removes or deletes nucleotides from one end of each strand of the heteroduplex nucleic acid molecules until it encounters said mismatch-binding protein bound to a mismatch site, said protein then acting to block further deletions and strand degradation by the exonuclease enzyme, said digestion being continued for a sufficient time to ensure that nucleic acid molecules not bound to said mismatch-binding protein are completely degraded; and (d) analyzing the nucleic acid digestion products from step (c) to determine the size or sizes of remaining single stranded nucleic acid fragments.

6. A method as claimed in claim 5 wherein step (d) is carried out by gel electrophoresis of nucleic acid digestion products from step (c) whereby nucleic acid fragments are separated according to their relative size.

7. A method as claimed in any of the preceding claims wherein a detectable label is incorporated in said non-mutant strands derived from the reference nucleic acid.

8. A method as claimed in claim 1 wherein the target nucleic acid and the reference nucleic acid are each subjected to PCR amplification in a preliminary stage before forming said heteroduplex nucleic acid molecules.

9. A method as claimed in claim 1 wherein the exonuclease enzyme has specific unidirectional exonuclease activity.

10. A method as claimed in claim 1 in which the mismatch-binding protein is MutS encoded protein.

11. A method as claimed in claim 1, in which the mismatch-binding protein is selected from the group consisting of HexA from *Streptococcus pneumoniae*, MutS from *E. coli*, MutS from | *Salmonella typhimurium*, MutS from A. Vinlandii, MSH 1 from *Saccharomyces cerevisiae*, HMSH2 from humans, MMSH2 from mouse, XMSH2 from Xenopus, and p160 from humans.

12. A method as claimed in claim 1 in which step d) is carried out under slightly alkaline conditions and in the presence of a divalent cation.

13. A method as claimed in claim 12 in which the slightly alkaline conditions are provided by a pH range of 8.0 to 8.5 and the divalent cation is $Mg^{++}$ at a concentration of at least 7mM (preferably about 8mM).

14. A method as claimed in claim 5 in which the enzyme is T7 DNA polymerase.

15. A kit comprising materials and reagents required for carrying out a method of detecting and locating nucleic acid mutations in accordance with one or more of the preceding claims, said kit including, in separate containers, an enzyme having exonuclease activity, a mismatch-binding protein (or proteins) capable of seeking out and selectively binding to base-pair mismatch sites in heteroduplex nucleic acid molecules and protecting said sites against digestion by said exonuclease enzyme, and appropriate buffer, together with instructions for use.

16. The kit of claim 15 which in addition contains reagents for carrying out a preliminary PCR amplification of a particular sequence of a target nucleic acid, said reagents including preselected primers, Taq polymerase enzyme, a mix of deoxynucleotides and buffers to provide the necessary reaction mixture for carrying out selective PCR amplification.

17. A method for screening or testing a human or animal subject for the presence of a suspected genetic defect or mutated gene related disease, said method comprising obtaining nucleic acid from said subject and using that nucleic acid as the target nucleic acid in carrying out a method of detecting and localizing a base mismatch or mutation in accordance with claim 1.

* * * * *